United States Patent
Caduff et al.

(10) Patent No.: US 9,713,447 B2
(45) Date of Patent: Jul. 25, 2017

(54) DEVICE FOR DETERMINING THE GLUCOSE LEVEL IN BODY TISSUE

(75) Inventors: Andreas Caduff, Zurich (CH); Mark Stuart Talary, Zurich (CH); Francois Dewarrat, Zurich (CH); Daniel Huber, Zurich (CH); Gianluca Stalder, Wildberg (CH)

(73) Assignee: BIOVOTION AG, Zurich (CH)

( * ) Notice: Subject to any disclaimer, the term of this patent is extended or adjusted under 35 U.S.C. 154(b) by 1592 days.

(21) Appl. No.: 12/084,392

(22) PCT Filed: Nov. 10, 2005

(86) PCT No.: PCT/CH2005/000666
§ 371 (c)(1),
(2), (4) Date: Feb. 3, 2009

(87) PCT Pub. No.: WO2007/053963
PCT Pub. Date: May 18, 2007

(65) Prior Publication Data
US 2009/0312615 A1    Dec. 17, 2009

(51) Int. Cl.
*A61B 5/00* (2006.01)
*A61B 5/053* (2006.01)
(Continued)

(52) U.S. Cl.
CPC .......... *A61B 5/6843* (2013.01); *A61B 5/0531* (2013.01); *A61B 5/14532* (2013.01);
(Continued)

(58) Field of Classification Search
CPC ......... A61B 5/0261; A61B 5/05; A61B 5/053; A61B 5/0531; A61B 5/0533; A61B 5/0537; A61B 5/1455; A61B 5/14532
(Continued)

(56) References Cited

U.S. PATENT DOCUMENTS 3,654,072 A    4/1972  Massa
4,509,531 A    4/1985  Ward
(Continued)

FOREIGN PATENT DOCUMENTS

DE    44 46 346    6/1996
DE    100 35 415   1/2002
(Continued)

OTHER PUBLICATIONS

M. Brischwein et al, "Functional cellual assays with multiparametric silicon sensor chips" *Lab Chip*, 2003, 3, 234-240.
(Continued)

*Primary Examiner* — Adam J Eiseman
(74) *Attorney, Agent, or Firm* — Ladas & Parry LLP

(57) ABSTRACT

The apparatus for the non-invasive glucose detection comprises an electrical detection device (2) for measuring the response of the tissue or blood to an electric field at low frequencies below 1 MHz and at high frequencies above 10 MHz. The former is primarily dominated by skin hydration and sweat, while the latter contains contributions from the current glucose level. Combining the two signals allows an increased degree of accuracy. The apparatus further comprises a force or acceleration sensor (4, 5), which allows to detect the pressure of the apparatus against the skin and/or quick movements. Further sensor modules, such as a temperature sensor (6) or alternative perfusion sensor (7), improve the accuracy of the measured result.

12 Claims, 7 Drawing Sheets

(51) Int. Cl.
*A61B 5/145* (2006.01)
*A61B 5/026* (2006.01)
*A61B 5/11* (2006.01)

(52) U.S. Cl.
CPC ............... *A61B 5/0261* (2013.01); *A61B 5/11* (2013.01); *A61B 5/721* (2013.01); *A61B 2560/0242* (2013.01); *A61B 2562/0219* (2013.01); *A61B 2562/0247* (2013.01)

(58) Field of Classification Search
USPC ........................................ 600/316, 342, 366
See application file for complete search history.

(56) References Cited

U.S. PATENT DOCUMENTS

| | | | |
|---|---|---|---|
| 4,679,426 | A | 7/1987 | Fuller |
| 4,765,179 | A | 8/1988 | Fuller et al. |
| 4,875,486 | A | 10/1989 | Rapoport et al. |
| 4,876,504 | A | 10/1989 | Blake et al. |
| 5,050,612 | A | 9/1991 | Matsumura |
| 5,072,732 | A | 12/1991 | Rapoport et al. |
| 5,077,476 | A | 12/1991 | Rosenthal |
| 5,119,819 | A | 6/1992 | Thomas et al. |
| 5,353,802 | A * | 10/1994 | Ollmar ........................ 600/547 |
| 5,508,203 | A | 4/1996 | Fuller et al. |
| 5,771,891 | A | 6/1998 | Gozani |
| 5,792,668 | A | 8/1998 | Fuller et al. |
| 5,890,489 | A | 4/1999 | Elden |
| 6,070,092 | A | 5/2000 | Kazama et al. |
| 6,070,093 | A | 5/2000 | Oosta et al. |
| 6,309,884 | B1 | 10/2001 | Cooper et al. |
| 6,356,776 | B1 | 3/2002 | Berner et al. |
| 6,442,408 | B1 | 8/2002 | Wenzel et al. |
| 6,487,906 | B1 | 12/2002 | Hock |
| 6,491,647 | B1 | 12/2002 | Bridger et al. |
| 6,517,482 | B1 | 2/2003 | Elden et al. |
| 6,565,509 | B1 | 5/2003 | Say et al. |
| 6,723,048 | B2 | 4/2004 | Fuller |
| 6,762,609 | B2 | 7/2004 | Alanen et al. |
| 6,763,256 | B2 * | 7/2004 | Kimball et al. ............. 600/336 |
| 6,841,389 | B2 | 1/2005 | Novikov et al. |
| 6,954,662 | B2 | 10/2005 | Freger et al. |
| 7,184,810 | B2 | 2/2007 | Caduff |
| 2002/0001202 | A1* | 1/2002 | Williams ............... A61B 17/02 362/572 |
| 2002/0106709 | A1 | 8/2002 | Potts et al. |
| 2002/0155615 | A1 | 10/2002 | Novikov et al. |
| 2003/0153821 | A1 | 8/2003 | Berner et al. |
| 2003/0181795 | A1 | 9/2003 | Suzuki et al. |
| 2003/0220581 | A1 | 11/2003 | Ollmar et al. |
| 2004/0039254 | A1 | 2/2004 | Stivoric et al. |
| 2004/0065158 | A1 | 4/2004 | Schrepfer et al. |
| 2004/0104736 | A1 | 6/2004 | Cohen et al. |
| 2004/0127780 | A1 | 7/2004 | Ollmar et al. |
| 2004/0133353 | A1 | 7/2004 | Geutebruck |
| 2004/0147819 | A1 | 7/2004 | Caduff et al. |
| 2004/0181141 | A1 | 9/2004 | Kislov et al. |
| 2004/0220485 | A1 | 11/2004 | Rytky |
| 2005/0043602 | A1 | 2/2005 | Freger et al. |
| 2005/0053523 | A1 | 3/2005 | Brooke |
| 2005/0070778 | A1* | 3/2005 | Lackey et al. ................ 600/366 |
| 2005/0083992 | A1 | 4/2005 | Pesach |
| 2005/0101846 | A1 | 5/2005 | Fine et al. |
| 2005/0113662 | A1 | 5/2005 | Djennati et al. |
| 2005/0171415 | A1 | 8/2005 | Hirao |
| 2005/0187471 | A1* | 8/2005 | Kanayama et al. .......... 600/437 |
| 2005/0192488 | A1 | 9/2005 | Bryenton et al. |
| 2005/0197555 | A1 | 9/2005 | Mouradian et al. |
| 2005/0203361 | A1 | 9/2005 | Caduff et al. |
| 2005/0203363 | A1 | 9/2005 | Caduff et al. |
| 2006/0025664 | A1 | 2/2006 | Kim et al. |
| 2006/0195022 | A1* | 8/2006 | Trepagnier et al. ......... 600/316 |
| 2006/0264730 | A1 | 11/2006 | Stivoric et al. |
| 2007/0282180 | A1 | 12/2007 | Caduff et al. |
| 2008/0057526 | A1 | 3/2008 | Caduff et al. |

FOREIGN PATENT DOCUMENTS

| | | |
|---|---|---|
| GB | 2 033 575 | 5/1980 |
| GB | 2 055 206 | 2/1981 |
| GB | 2 100 864 | 1/1983 |
| JP | 62-83649 | 4/1987 |
| JP | 9-201337 | 8/1997 |
| JP | 2000-162176 | 6/2000 |
| JP | 2001-500392 A | 1/2001 |
| JP | 2004-298408 A | 10/2004 |
| RU | 2 073 242 | 2/1997 |
| RU | 2 088 927 | 8/1997 |
| WO | 93/18395 | 9/1993 |
| WO | 93/18402 | 9/1993 |
| WO | 97/39341 | 10/1997 |
| WO | 98/04190 | 2/1998 |
| WO | 98/09566 | 3/1998 |
| WO | 99/44495 | 9/1999 |
| WO | 00/09996 | 2/2000 |
| WO | 01/26538 | 4/2001 |
| WO | WO 01/26538 * | 4/2001 |
| WO | WO 02/069791 * | 9/2002 |
| WO | 2004/016170 A1 | 2/2004 |
| WO | 2004/023125 | 3/2004 |
| WO | 2005/017642 A2 | 2/2005 |
| WO | 2005/053523 | 6/2005 |
| WO | 2005/053523 A1 | 6/2005 |
| WO | 2005/057168 A2 | 6/2005 |

OTHER PUBLICATIONS

Z. Wang et al, "Measurements of scattered light on a microchip flow cytometer with integrated polymer based optical elements" *Lab Chip*, 2004, 4, 372-377.

S. Gawad et al; "Micromachined impedance spectroscopy flow cytometer for cell analysis and particle sizing" *Lab on a Chip*, 2001, 1, 76-82.

S. Gawad et al; Dielectric spectrsocopy in a micromachined flow cytometer: theoretical and practical considerations *Lab Chip*, 2004, 4, 241-251.

English-language Examination Report dated Apr. 24, 2012 in respect of Application No. 10 015 557.1-2319.

English abstract of DE 100 35 415 dated Jan. 31, 2002.

English translation of Abstract and Description of DE 4446346 dated Jun. 27, 1996.

Patent Abstracts of Japan of JP 9-201337 dated Aug. 5, 1997.

Patent Abstracts of Japan of JP 2000-162176 darted Jun. 16, 2000.

Patent Abstracts of Japan of JP 62-083649 dated Apr. 17, 1987.

English Abstract of RU 2 073 242 dated Feb. 10, 1997.

English Abstract of RU 2 088 927 dated Aug. 27, 1997.

Tenhunen, J., et al. "Non-invasive glucose measurement based on selective near infrared absorption; requirements on instrumentation and spectral range." *Measurement* 24 (1998) pp. 173-177.

Khalil, O.S. "Non-Invasive Glucose Measurement Technologies: An Update from 1999 to the Dawn of the New Millennium." *Diabetes Technology & Therapeutics* (2004) vol. 6, pp. 660-695.

Choleau, C., et al. "Prevention of Hypoglycemia Using Risk Assessment With a Continuous Glucose Monitoring System." *Diabetes* (2002) vol. 51, pp. 3263-3273.

Feldman, Y., et al. "Time domain dielectric spectroscopy: An advanced measuring system." *Rev. Sci. Instrum* (1996) vol. 67, No. 9, pp. 3208-3216.

Feldman, Y. D., et al. "Time domain dielectric spectroscopy. A new effective tool for physical chemistry investigation." *Colloid & Polymer Science* (1992) vol. 270, No. 8, pp. 768-780.

Mamishev, A.V., et al. "Uncertainty in Multiple Penetration Depth Fringing Electric Field Sensor Measurements." *IEEE Transactions on Instrumentation and Measurement* (2002) vol. 51, No. 6, pp. 1192-1199.

European Search Report dated Sep. 7, 2011 for Application No. EP 10015557.1-2319.

A. Caduff et al., First human experiments with a novel non-invasive, non-optical continuous glucose monitoring system, Biosensor and Bioelectronics 19 (2003), 209-217.

(56) References Cited

OTHER PUBLICATIONS

Japanese office action dated Apr. 26, 2011 in respect of Japanese Patent Application No. 2008-539204.
Espacenet English abstract of JP 2001-500392 A.
Espacenet English abstract of JP 2004-298408 A.

* cited by examiner

DEVICE FOR DETERMINING THE GLUCOSE LEVEL IN BODY TISSUE

TECHNICAL FIELD

The present invention relates to the determination of glucose levels in body tissue/blood and various concepts for improving the accuracy of the same.

BACKGROUND ART

WO 2005/053523 and WO 2005/053526 describe various aspects of a non-invasive, in-vivo technique for determining the glucose level in body tissue. The technologies described in these documents do provide a reasonable degree of accuracy, but long-term accuracy can only be achieved using strict control of the parameters under which the measurement takes place, which may be undesirable in some situations.

DISCLOSURE OF THE INVENTION

Hence, it is a general object of the invention to provide ways to improve the accuracy of in-vivo non-invasive glucose determination.

This object is achieved by the means described in any of the independent claims.

According to a first aspect of the invention, an apparatus is described comprising an electrical as well as an optical detection device. The electrical detection device has an electrode arrangement which is suited to apply an electric field to the body tissue for measuring at least one first parameter describing a response of the tissue to said electric field. The optical detection device comprises a light source and a light receiver for measuring at least one second parameter describing a transmission or reflection of light by said tissue. The apparatus is further equipped with evaluation circuitry for determining the glucose level from a combination of the first and second parameters. By combining a parameter obtained from the electric field response and another parameter obtained from the optical response, it becomes possible to eliminate or, at least, reduce the dependence of the signal from the blood perfusion level in the tissue under study.

In a second aspect of the invention, the apparatus contains a detection device for non-invasively measuring a glucose parameter of the tissue, which glucose parameter depends on the glucose level. This detection device can e.g. be based on a dielectric measurement and/or an optical measurement. In addition to the detection device, the apparatus comprises a force sensor for measuring a force parameter indicative of the force by means of which said apparatus is pressed against the tissue as well as evaluation circuitry for determining the glucose level. This allows an increased accuracy since the parameters measured by non-invasive methods for glucose determination generally depend on the force by means of which the apparatus is pressed against the tissue. Hence, by measuring the force parameter, the result from the glucose parameter can be corrected and/or an alert can be issued if the apparatus is not properly pressed/attached against the tissue or a biophysical change has occurred in the body that causes a large increase in the applied pressure such as water retention, blood pressure change fluctuations.

In a third aspect, closely related to the second aspect of the invention, the apparatus comprises a detection device for non-invasively measuring a glucose parameter of the tissue depending on the glucose level. This detection device may again be based e.g. on a dielectric measurement and/or an optical measurement. The apparatus further comprises an acceleration sensor for measuring an acceleration of tie apparatus as well as evaluation circuitry for determining the glucose level. This combination of features is based on the understanding that during an acceleration of the apparatus/body (as it may e.g. occur when wearing the apparatus on an arm and moving the arm, the force by means of which the apparatus is pressed against the tissue varies, which either requires a correction of the measurement obtained from the detection device and/or a suppression of at least part of the functions of the apparatus and/or makes it advisable to issue an alert to the user. This can also indicate periods of time when there is a greater confidence of measuring changes associated with glucose rather than movement in the evaluation algorithm such as sleep, desk work or driving where limited movement is expected.

In a fourth aspect, the apparatus comprises an electrical detection device having an electrode arrangement for applying an electric field to the tissue. The detection device is adapted to measure at least one first parameter at a frequency of the field above 10 MHz and at least one second parameter at a frequency of the field below 1 MHz.

The apparatus further comprises evaluation circuitry for determining the glucose level from the combination of the first and the second parameter.

This is based on the understanding that the first parameter will depend on the glucose level as well as sweat, and the skin hydration while the second parameter primarily depends on skin hydration only. Hence combining the two parameters, e.g. using calibration data, allows to reduce the dependency of the result on skin hydration.

BRIEF DESCRIPTION OF THE DRAWINGS

The invention will be better understood and objects other than those set forth above will become apparent when consideration is given to the following detailed description thereof. Such description makes reference to the annexed drawings, wherein.

MODES FOR CARRYING OUT THE INVENTION

1. Overview

Figure 1:
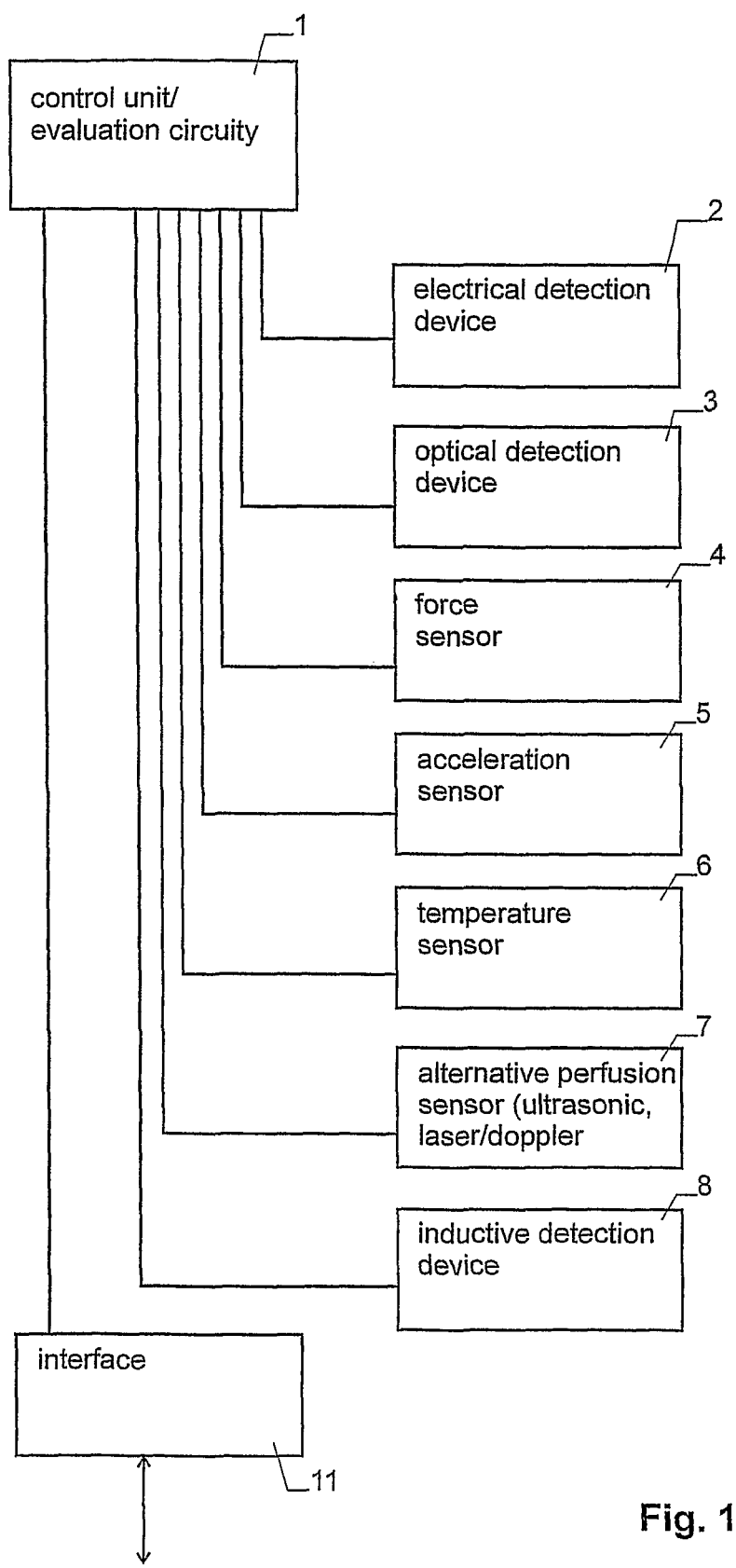
FIG. 1 is a block circuit diagram of an apparatus embodying the various aspects of the invention.

FIG. 1 shows an overview of an embodiment of an apparatus illustrating the various aspects of the present invention.

As can be seen, the apparatus comprises a control unit and evaluation circuitry 1, which can e.g. be implemented as a microprocessor, peripheral circuitry and software components suited for carrying out the various tasks described below. In addition, the apparatus comprises various sensor modules 2-8:

An electrical detection device 2 has electrodes for applying an electrical field to the tissue of the user and measures at least one parameter describing the response of said tissue to said electric field.

An optical detection device 3 has a light source and a light receiver for measuring at least one parameter describing a transmission or reflection of light by the tissue.

A force sensor 4 is designed to measure a force parameter indicative of the force by means of which the apparatus is pressed against the tissue or between the apparatus and underlying tissue or its distribution over a surface in the case of a flexible sensing element or measured tissue.

An acceleration sensor 5 measures the acceleration (including deceleration) of the apparatus.

A temperature sensor 6 (or, advantageously, several temperature sensors) are used to measure one or more temperature values. They are e.g. used to measure the temperature on the surface of the tissue, in the apparatus or of the environment.

An alternative perfusion sensor 7 can e.g. be provided (in addition to or instead of some other sensor modules) for measuring a parameter depending on the level of blood perfusion of the tissue.

An inductive sensor 8 can be used for measuring an inductive response of the tissue, i.e. the response of the tissue to an applied magnetic field.

This list of sensor modules is not exhaustive. The apparatus may also be equipped with other sensor modules that allow a (advantageously non-invasive) determination of a parameter that has an influence on the measured glucose level. Also, one or more of the sensor modules can be omitted if the corresponding parameter(s) is (are) to be ignored. Finally, some of the modules may be combined into one: For example, the force and acceleration sensors may be combined in a single module because both basically measure a force or a distribution of a force over a surface.

Finally, the apparatus is advantageously also equipped with an interface 11 for connecting the control unit 1 to external data processing and/or control circuitry.

In principle, the operation of the apparatus is as follows: Control unit/evaluation circuitry 1 operates the various sensor modules 2-8 (or part thereof) to measure a number of parameters that depend on the user's state (e.g. electric and optical response of the tissue), the state of the user's surroundings (e.g. ambient temperature), as well as on the state of the apparatus itself (e.g. the temperature within the apparatus). Evaluation circuitry 1 combines the various measured parameters, e.g. using multidimensional calibration data and/or algorithmic rules, to calculate a signal or display a value indicative of the glucose level.

Figure 2:
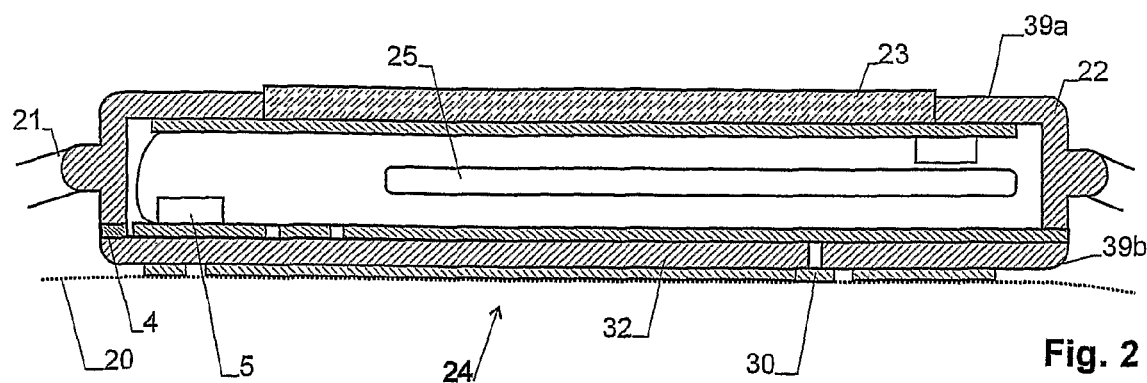
FIG. 2 is a sectional view of an embodiment of the apparatus.

A possible mechanical set-up of the apparatus is shown in FIG. 2. The shown apparatus has approximately the shape and size of a wristwatch and can be worn on an arm or leg 20 by means of a wristband 21. It has a housing 22 with a first housing part 39a and a second housing part 39b. A unit 23 is located at its front side and an electrode arrangement 24 at its backside. The interior of the housing provides space for the circuitry of the control unit and evaluation circuitry 1, at least part of the various modules 2-8 as well as a battery 25. It must be noted, though, that this is merely one advantageous example of a possible embodiment. Other designs can be used as well. For example, part or all of control unit and evaluation circuitry 1 may be arranged in a separate device connected to the apparatus of FIG. 2 by wirebound or wireless communication means.

Instead of using a wristband 21, the apparatus can also be attached to the body by other means, such as adhesive tape.

In the following, the various parts of the apparatus of FIGS. 1 and 2 will be described in more detail.

2. Electrical Detection Device

Electrical detection device 2 serves to measure the response of the tissue to an electric field, which can e.g. be expressed in terms of the (complex) electrical impedance or in general dielectric characterization. The field is applied to the tissue by means of one or more electrode arrangements.

In the present embodiment, the impedance (or a value correlated to the same) for field frequencies above 10 MHz measured by the electrical detection device is the one measured parameter that has the strongest dependence on glucose or variations thereof of all measured parameters and is therefore also termed the "glucose parameter". If, however, in another embodiment, glucose is primarily determined by optical means, an optically measured parameter may be termed the "glucose parameter". The "glucose parameter" may also be obtained from a combination of various measurements, e.g. from a combination of optical and dielectric measurements.

Turning back to the present embodiment, the impedance measurement of the skin tissue can be made using a variety of sensors that can operate as stand alone devices or combined structures. They can be attached to multiple positions on the body to allow for the differences in the micro vascularisation of the tissue associated with the different regions to be examined. For example, since the degree of micro vascularisation increases as the blood vessels move towards extremities of the body (i.e. hands and feet) a greater relative sensitivity to dielectric changes in blood is achieved in such tissues. At the earlobes, for example, there is the advantage that they possess the greatest degree of blood perfusion for capacitively coupled measurements to be made, however there are obvious restrictions on the size of the tissue surface area available and the movement that occurs in such a position.

2.1 Differential Sensor

In an advantageous embodiment, the electrical detection device 2 comprises a differential sensor having several arrangements of electrodes that differ in their geometry. This is explained in the following.

The human skin can be seen as several corrugated parallel layers with various physical properties and biological functions. The dermis layer is the one with lightest blood perfusion, hence it is believed to be most sensitive to blood glucose changes. As it is situated below other layers (for example epidermis and stratum corneum), a direct measurement of dielectric properties of the dermis layer is not possible with a non invasive sensor placed on the skin surface. The purpose of the differential sensor is then to achieve depth specific measurements in order to distinguish impacts of the various layers on the measurement of the whole volume under consideration.

The method that is chosen here uses multiple electrode arrangements with different geometries, e.g. different widths and separations. Generally speaking, the penetration depth of the signal increases with increasing electrode width and electrode separation. For a multilayer system, there is a maximum of sensitivity to the magnitude of the dielectric changes for each layer at different electrode widths and separations. Combining the results of the measurements from the different electrode arrangements allows to track contributions of the separate layers. Finite element modeling simulations of the electric potential distribution allow the geometry of the sensor to be optimized and to achieve maximum sensitivity to changes in the dielectric properties of the specific layers.

For example a sensor consisting of two arrangements of electrodes can be considered. One electrode arrangement is called short sensor. The small size and separation of electrode make it sensitive to changes in upper skin layers. The second set is called long sensor. The large size of the electrode and the large gap make it sensitive to deeper layers, in this case dermis.

Figure 3:
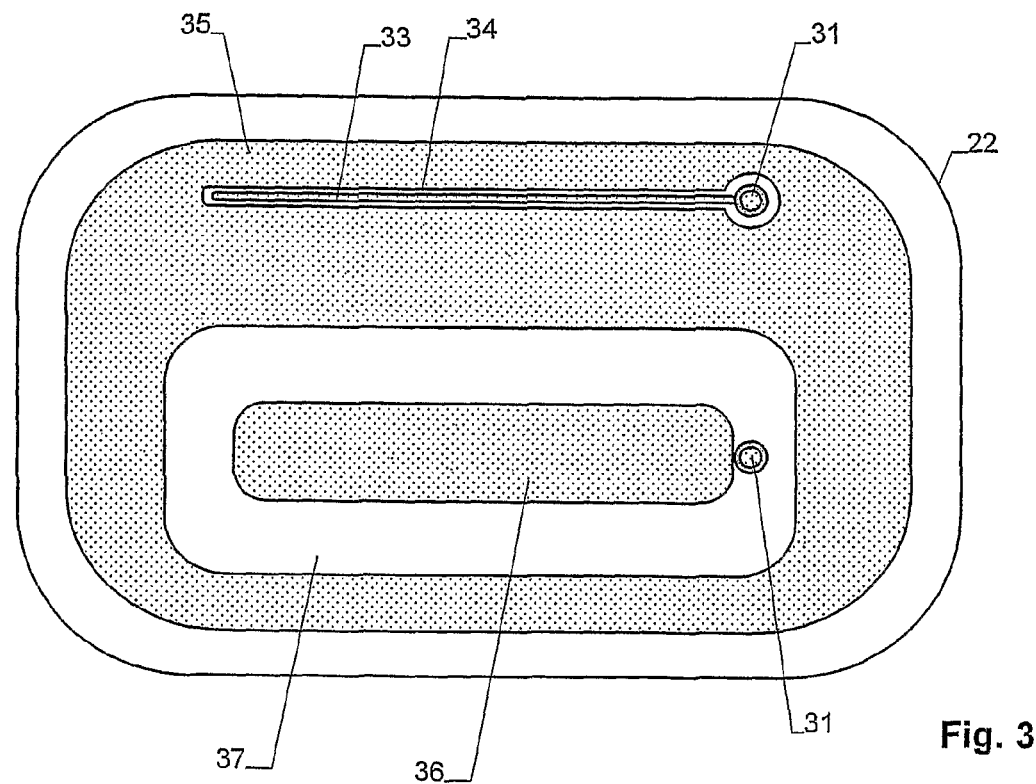
FIG. 3 shows the layout of the electrodes of the embodiment of FIG. 2, FIG. 4 a possible circuit diagram for driving the electrodes of the embodiment of FIG. 3.

FIG. 3 shows an example of such a sensor. The dotted areas represent the electrodes, the circles the contacts 31 through the base 32 that the electrode arrangements are mounted on.

The first electrode arrangement comprises a thin strip electrode 33 separated by a thin gap 34 from a base electrode 35. The second electrode arrangement comprises a thicker strip electrode 36 separated by a thicker gap 37 from the base electrode 35. In other words, the two electrode arrangements have a common first electrode, namely the base electrode 35.

Base electrode 35 can e.g. be applied to ground, while the strip electrodes 33 and 36 carry an AC signal.

The first electrode arrangement is sensitive to the properties of the upper skin layers. The second electrode arrangement is larger and has larger distance to ground in order to be sensitive to the properties of a deeper skin layer, in this case dermis.

The circuitry for driving each of the electrode arrangements and retrieving signals therefrom may e.g. be the same as disclosed (for a single electrode arrangement) in WO 2005/053523, which is incorporated herein in its entirety by reference. However, part of that circuitry would have to be duplicated to drive the two electrode arrangements.

Figure 4:
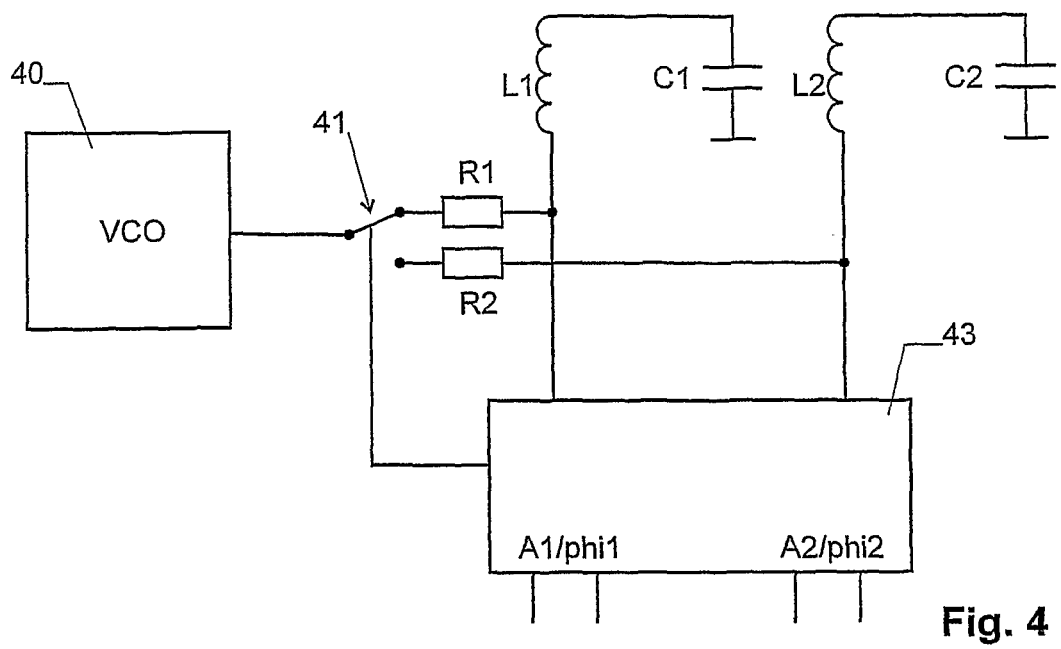

A possible design of the circuitry for driving the two electrode arrangements is shown in FIG. 4. As can be seen, the circuitry comprises a (signal generating element) voltage controlled oscillator (VCO) 40, which generates an AC voltage of variable frequency. The frequency can e.g. be set by control unit 1. The signal from VCO 40 is fed to a switch 41, which alternatively feeds it to either the first electrode arrangement (denoted by C1) or the second electrode arrangement (denoted by C2) via known resistors R1, R2 and inductances L1 and L2, respectively. For each path, the voltage at the point between the resistors (R1 or R2) and the inductance (L1 or L2) is fed to a measuring circuit 43, which measures its phase phi1 or phi2 as well as its amplitude A1 or A2. These measured signals are further processed in the control unit and evaluation circuitry 1.

It must be noted that the circuit shown in FIG. 4 is merely one of many possible embodiments of such a circuit. In particular, the measurement may also be carried out in the time domain (e.g. using short pulses), e.g. with subsequent Fourier analysis. Such a device has been described in WO 04/021877.

Further processing of the signals will, in general terms, comprise the step of comparing the signals obtained by the two electrode arrangements, e.g. by calculating a difference or ratio of the amplitudes, potentially after weighing the signals with suitable weights.

A general algorithm and method of calibration to be used for evaluating the signals of the electrical detection device 2 (and, in fact, for the signals of all measurement modules 2-8) is described in WO 2005/053526.

In an alternative embodiment, the layout of FIG. 3 could be replaced by a design where the first and second electrode arrangements have a larger extent of spatially overlapping fields, e.g. by using three or more adjacent strip electrodes between ground electrodes, wherein the central strip electrode is either applied to ground (for forming the first electrode arrangement) or to the same signal as the other strip electrodes (for forming the second electrode arrangement). Switch 41 would in that case be replaced by a suitable array of switching allowing to connect individual strip electrodes either to ground or to the signal from VCO 40. The apparatus would be operated to carry out a measurement for each electrode arrangement and then compare the two results.

An electrode design consisting of parallel strip electrodes will also be shown in the next section.

The frequency of the signals used in the differential sensor is advantageously above 10 MHz, e.g. in the range of some ten MHz up to several GHz. As described in WO 2005/053523, measurements in this frequency range are particularly sensitive to the glucose concentration or variations thereof.

2.2 Moisture and Sweat Sensor

The present apparatus can further comprise a moisture/sweat sensor that measures the sweat (surface water content) of the skin. This is an import parameter that affects the dielectric and electric response of the skin without being a direct measure of the glucose content. Hence, a more accurate knowledge of the skin hydration and sweat allows to obtain a more accurate result.

Advantageously, the skin hydration is also measured by the electrical detection device, since it strongly affects the electrical properties of the skin.

For measuring skin hydration, the electrical detection device can either use the same electrodes as for measuring the electric and dielectric response of the tissue as the primary glucose sensor (i.e. the differential sensor in the present embodiment), or it can use separate electrodes. In both cases, it measures the impedance between the electrodes.

The impedance measurement is based on a capacitance measurement of a dielectric medium similar to the differential sensor but is carried out at much lower frequencies, advantageously at a fixed frequency below 10 MHz, in particular below 1 MHz, or using a wide frequency sweep at signal frequencies in the range of 1 kHz-10 MHz. Equivalently, a single pulse with frequency contributions in this range can be used, advantageously with subsequent digital and/or analog filtering for frequencies outside the range. Any change in the dielectric constant due to skin surface hydration variation alters the capacitance of a precision measuring capacitor. The measurement can detect even slightest changes in the hydration level. The reproducibility of the measurement is very high and the measurement time is very short (1 s). When using closely spaced, small electrodes, the measurement depth can be very small (100 µm). It can be varied depending on the sensor geometry. The resistance of the skin surface at low frequencies is measured. This type of measurement is similar to the widely used Galvanic Skin Response (GSR) detection.

Advantageously, two measurements are carried out. A first one is carried out at preferably between approximately 1 kHz and 100 kHz to provide a first parameter, a second one preferably between approximately 100 kHz and 1000 kHz to provide a second parameter. The first measurement at approximately 1 kHz has been found to depend primarily on surface sweat, whereas the measurement at and above 100 kHz is primarily due to the hydration of lower skin layers. By measuring at both frequencies, a better knowledge of the system can be gained.

2.3 Signal Generation

Generating the various signals used by the electrode arrangements of electrical detection device 2 is straightforward. Depending on the frequency and frequency range, the signal voltages may be produced in simple LC- or microwave oscillators, oscillators controlled by a phase locked loop (PLL) and associated circuitry (i.e. mixers, frequency dividers, superposition of a number of signal frequencies etc.) or through direct digital synthesis (DDS, sometimes termed NCO—numeric controlled oscillator). All these systems are able to produce frequencies from zero up to about 100 GHz. Signal sources are available commercially from a plethora of vendors, either as electronic parts or as complete assembled and tested units.

Key parameters for such signal sources are frequency range, frequency and amplitude stability. For portable devices power consumption is also a very important figure.

Measurements can be carried out in a frequency range between some kHz up to and exceeding 350 GHz. Sometimes more than one electrode arrangement may be used for one frequency or a range of frequencies. Also different electrode arrangements may be positioned differently with respect to the tissue region of interest.

2.4 Conclusion

As described, the electrical detection device 2 measures at least two parameters. The first parameter describes the response of the tissue to a field generated by the electrode arrangement at a frequency of the field above 10 MHz. The second parameter describes the response of the tissue to the field generated by the electrode arrangement at a frequency of the field below 1 MHz. Since the first parameter depends strongly on glucose, but also on skin hydration, while the second parameter depends primarily on skin hydration, combining the two in evaluation circuitry 1 allows to decrease the dependence on skin hydration.

3. Optical Detection Device

Optical detection device 3 is primarily aimed at determining and quantifying changes in blood flow and the perfusion characteristics in a defined volume of skin and underlying tissue or generally to allow generating a measure for perfusion and volume fraction changes in the spatial volume under study. There are many factors associated with physiological changes of the body that can change the blood perfusion level in the skin tissue. A sensor that combines an optical detector with the signals from electrical detection device 2 has the added advantage that an independent measure of blood volume and flow can be used to account for corresponding variations of the signal from the electrical detection device 2. It is useful to have different measures of such perturbing factors for compensation purposes The sensor aims to measure blood flow and perfusion so that this additional parameter can be extracted and used to compensate the influence of changes in microvascular flow. In addition, the signal can serve as an additional parameter to improve the accuracy of the apparatus.

Implementations of optical detection device 3 include a light source, e.g. in the broadband visible spectrum, combined with a light detector to measure reflectance and/or absorbance of the radiation by the tissue volume. The separation distance between the transmitter and receiver can determine the volume of skin tissue being monitored and the depth of penetration of the incident waves. Large separation tends to allow for greater sensitivity of the sensor at greater penetration depths. The light source can be incorporated into the apparatus or driven from an external source by using optical waveguide technology to determine the exact transmission path of the radiation within the tissue. Similarly the radiation can be sensed directly by discrete components in the apparatus itself, or be extracted via the waveguide system to an external sensor.

Variation in penetration depth measurement within an integrated sensor structure can be achieved by a combination of multiplexing the input and output signals from the waveguide structure for example, to vary the separation distance between the illuminated waveguide and the receiving waveguide. The optical detection device could e.g. comprise an external light source and detection system coupled to the waveguide via an optical waveguide, or could integrate the light source into the sensor apparatus itself, e.g. by using light emitting polymers in the fabrication of the sensor. The opto-active polymers can form the supporting structure of the electrode arrangements of electrical detection device 2, which has the advantage that this would enable the direct coupling of the two measured signals into the same tissue volume. The sensing component of the sensor can consist of a single photodiode element or an array of sensing elements that can also be used to reveal change in reflection characteristics of the underlying tissue according to varying penetration depth or the distribution characteristics over the measured surface.

The light source can generate narrowband light or a multitude of specific spectral bands chosen to match the absorption and reflection characteristics of the underlying tissue and fluids, or include a broadband spectrum. In the example of a CCD array, a broad spectrum response could be achieved combined with spatial separation information.

Figure 5:
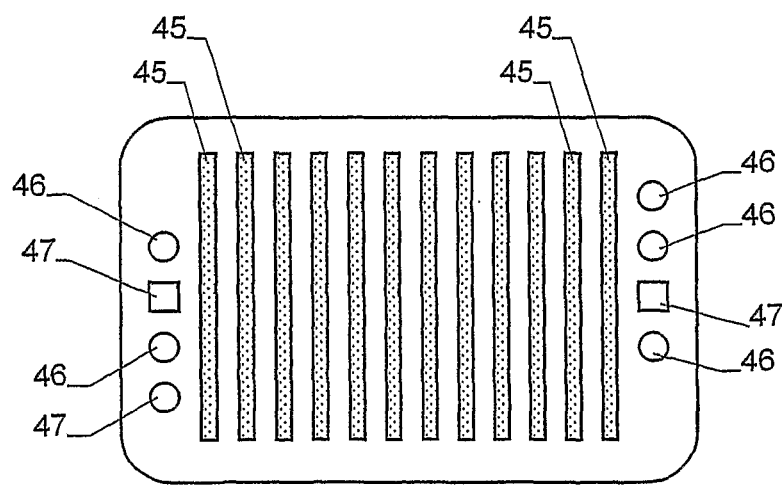
FIG. 5 is a second embodiment of the layout of the electrodes, together with the arrangement of light sources and light detectors.

A specific embodiment of the optical detection device 3 together with an arrangement of strip electrodes 45 (as an alternative to the arrangement of FIG. 3) is shown in FIG. 5.

As mentioned above, the strip electrodes 45 can e.g. be operated in a first electrode arrangement where the even electrodes are applied to ground and the odd electrodes to the signal and in a second electrode arrangement where the first two electrodes are applied to ground, the second two electrodes to the signal, the third two electrodes to ground, etc.

As can be seen, the apparatus of FIG. 5 further comprises a number of light sources 46 associated with light detectors 47. For example, two or three light sources 46 can be arranged in close proximity to a light detector 47, which allows to use light sources of different wavelength and/or light sources at different distances from the light detectors.

The light sources 46 can e.g. be light emitting diodes and the light detectors can e.g. be photodiodes.

Figure 6:
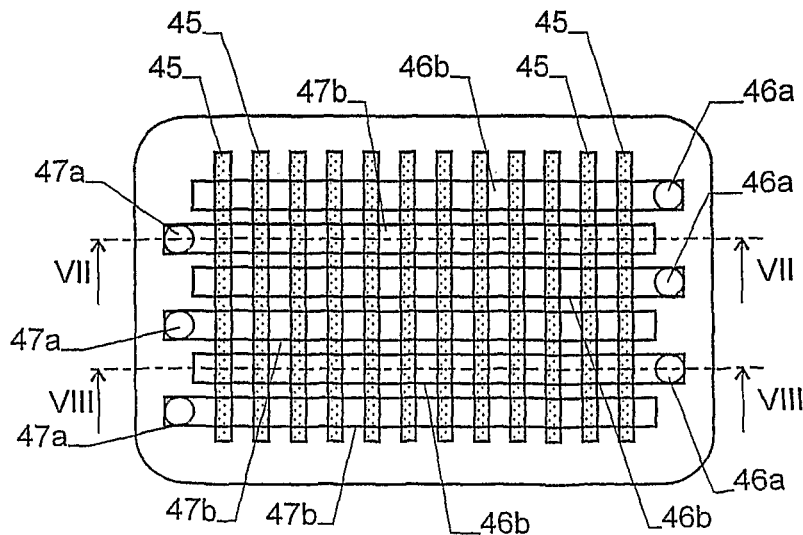
FIG. 6 is a third embodiment with a different arrangement of light sources and light detectors.
Figure 7:
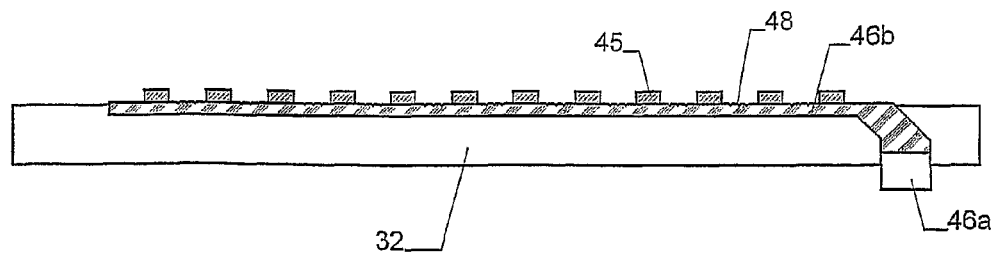
FIG. 7 is a sectional view along line VII-VII of FIG. 6.
Figure 8:
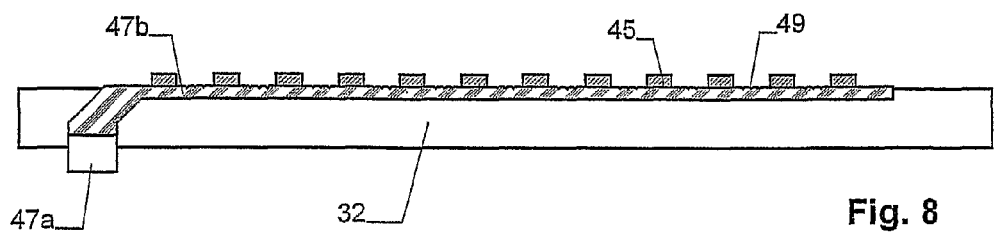
FIG. 8 is a sectional view along line VIII-VIII of FIG. 6.

Another embodiment of the apparatus is shown in FIGS. 6-8. It again comprises a plurality of parallel strip electrodes 45 and is equipped with light sources and light detectors. In this case, however, the light sources are located below the electrode arrangement and transmit their light through the electrode arrangement, namely through the gaps between the adjacent strip electrodes 45. The light detectors are also located below the electrode arrangement and receive light reflected from the tissue and transmitted through the electrode arrangement.

Each light source comprises, in this embodiment, a light emitter 46a and a waveguide 46b. The light source is arranged to emit its light into the waveguide 46b, while the waveguide is provided with surface gratings or roughed areas 48 in the gaps between the strip electrodes 45, which decouple the light from the waveguide 46b and emit it into the tissue.

Similarly, each light detector comprises a light sensor 47a and a waveguide 47b. The waveguide 47b is substantially of the same design as the waveguide 46b and has surface gratings or roughed areas 49 in the gaps between the strip electrodes 45. Light reflected from the tissue is scattered on the gratings or roughed areas 49 and coupled into the waveguide 47b, from where it is projected onto light sensor 47a.

In the embodiment of FIGS. 6-8, the electrode assembly is substantially planar with a first surface facing the tissue and a second surface facing away from the same. The waveguides 46b and 47b are located at the second surface.

Instead of using waveguide light detectors as shown in FIG. 8, a CCD camera can be arranged below the electrodes, which allows to receive a spatially resolved image of the reflected light for better interpretation of the data.

3.1 Wavelength

Figure 9:
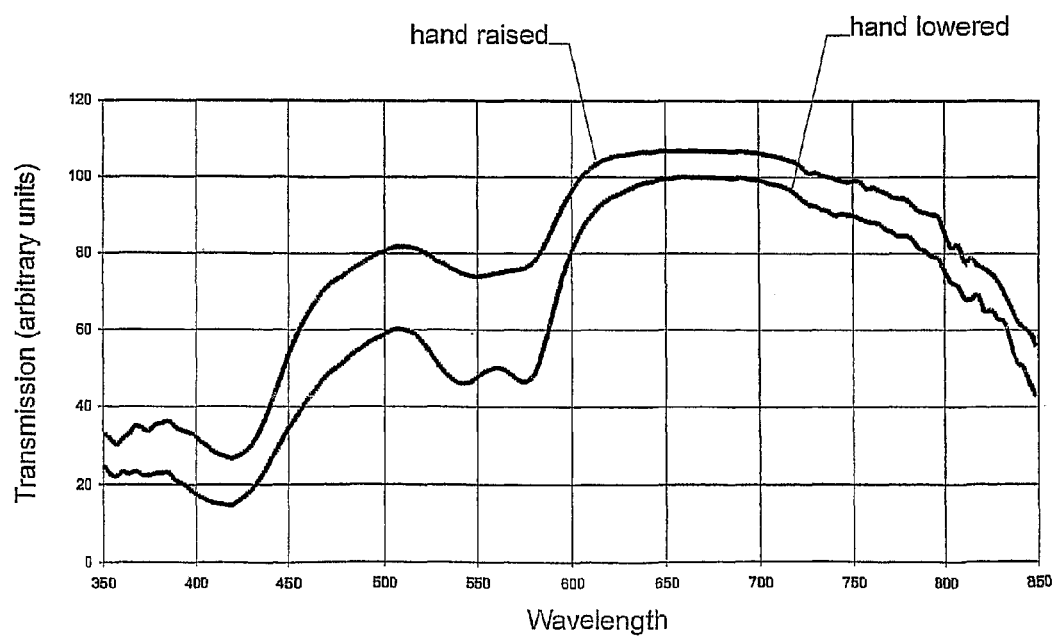
FIG. 9 shows the optical transmission at a fingertip for raised and lowered positions of the hand.

As mentioned, the main purpose of the optical detection device 3 is to give a measure of the blood perfusion of the tissue. To analyze the wavelengths that allow a sensitive measurement of the perfusion, an experiment was performed using a micro spectrometer with a scanned frequency range from 850 nm to 350 nm (Böhringer Ingelheim Microparts GmbH, Dortmund, Germany). Transmission at the finger tip was measured with different positions of the hand (raised and hanging down) to induce changes in the perfusion characteristics. A respective graph is presented in FIG. 9.

Wavelengths in the range of 450 to 800 nm, in particular of 550 and 700 nm, have been identified to allow the most efficient blood perfusion measurements of the upper and lower dermal vascular bed including bigger blood vessels.

It is known that NIR light can be used as well to monitor perfusion characteristics in deeper underlying tissues (muscle/fat layers etc), while the green wavelength (550 nm) is more characteristic for absorbance by blood and hence changes in the microvascular system.

Using combinations of measurements at several wavelengths and/or for several separations allows to refine the data on the perfusion characteristics from various dermal and generally tissue layers. Differences in temporal responses in different depths can also be extracted.

In one advantageous embodiment, measurements preferably at least in two wavelengths are carried out, one in the visible range of the spectrum (450 nm to 800 nm) and one in the near infrared (800 nm to 10 μm).

4. Force Sensor, Acceleration Sensor

The force and acceleration sensors are aimed at determining and/or quantifying the magnitude of changes in the response of electrical detection device 2 (or other sensor modules) caused by physical movements of the tissue being monitored or caused by a change of the pressure between the apparatus and the tissue.

One possible embodiment of a force sensor is shown in FIG. 2. In this embodiment, the lower housing part 39b, namely base 32 resting against the tissue, is suspended on the upper housing part 39a on one side only, while a piezoelectric force sensor 4 is arranged between its other end upper housing part 39a. An increase of the pressure of upper housing part 39a towards the tissue will lead to an increase of the force that is measured by force sensor 4.

The force measured by force sensor 4 is also a measure of the force exerted by wristband 21. An additional or alternative force sensor could also be applied to wristband 21 directly.

Advantageously, as in FIG. 2, housing 22 comprises a first housing part 39a and a second housing part 39b. The wristband is attached to the first housing part 39a and the force sensor is adapted to measure the force between the two housing parts.

Figure 10:
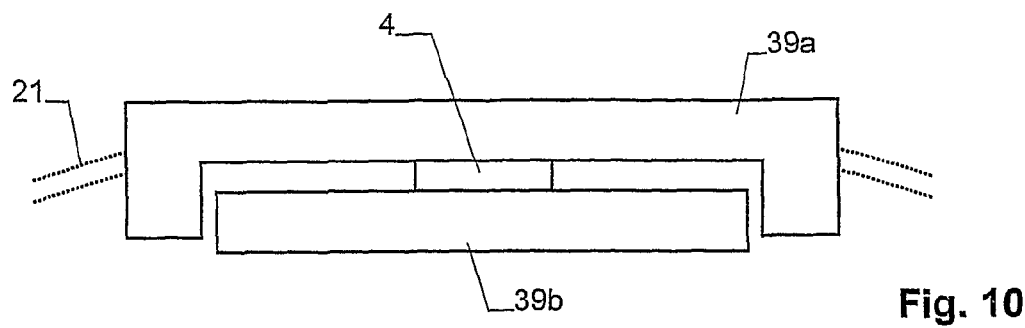
FIG. 10 shows a first possible arrangement of the force sensor.
Figure 11:
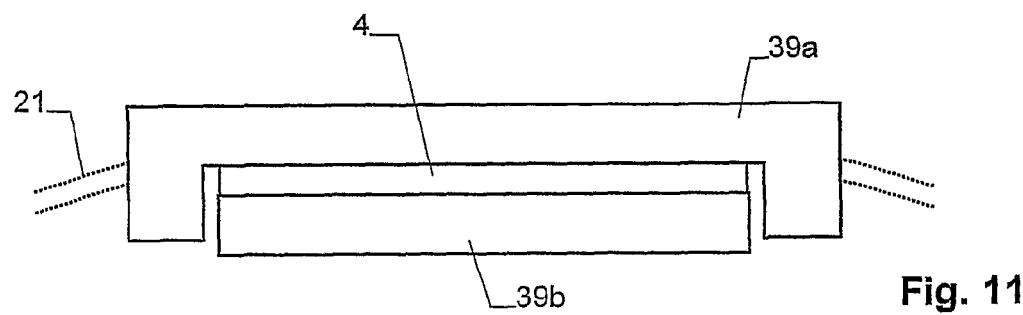
FIG. 11 shows a second possible arrangement of the force sensor.

Alternative embodiments where the force sensor 4 is attached between a first housing part 39a and a second housing part 39b are shown schematically in FIGS. 10 and 11. In both cases, first housing part 39a is connected to wristband 21, while second housing part 39b carries the non-invasive glucose detector, e.g. the electric detection device 2.

In the embodiment of FIG. 10, force sensor 4 is a small load cell arranged at the center between the two housing parts while, in the second embodiment of FIG. 11, force sensor 4 is an extended layer of pressure sensing material.

The pressure or force sensor 4 is aimed at determining and quantifying the magnitude of changes in the response of the apparatus associated with attachment and contact pressure of the apparatus on the tissue using e.g. the piezoelectric effect. The force sensor(s) can be incorporated into the housing of apparatus for measuring the changes in the force exerted on the tissue by the sensor relative the housing, or they measure the external force applied by the attachment of the device on the tissue. Such a measurement will provide a measure of the temporal changes in attachment pressure of the apparatus on the tissue related to movement and temporal physiological changes. Other implementations of such a sensor could include an indirect measurement of the pressure exerted by using electrostrictive materials integrated into the sensor substrate.

It is believed that blood flow in the skin has an influence on the measured signal in the apparatus. The force sensor can be used to detect if changes in the physical pressure of the apparatus on the tissue provides a disturbance to the measured impedance signal. It can provide an additional parameter that can be extracted and used to compensate for changes in the applied pressure and thus serve as an additional parameter to improve the accuracy of the apparatus, and/or it can provide a means for detecting unsuitable measurement conditions.

Instead of, or in addition to, a simple force sensor 4, an acceleration sensor 5 can be mounted in housing 22 (e.g. in the position indicated in FIG. 2) to measure the amount and direction of acceleration experienced by the apparatus and tissue.

Both velocity and direction information can be established as well as the rate of change of these parameters to indicate what physiological changes might be occurring in the measured tissue.

It is believed that blood flow in the skin has an influence on the measured signal in the apparatus. The force and/or acceleration sensors can be used to measure whether physical movement at the time when tissue measurements are being made are influenced by changes in the blood flow. The force and/or acceleration sensors can therefore provide an additional parameter to compensate for the influence of changes in microvascular flow and thus improving the accuracy of the apparatus.

The control unit/evaluation circuitry 1 is adapted to determine the glucose concentration from a combination of the parameter measured by the electrical detection device 2 and the signal from force sensor 4 and/or the acceleration sensor 5 as well as from the other sensor modules.

In an advantageous embodiment, the apparatus is adapted to suppress at least part of its operation and/or issue an alert if fluctuations of the signal from force sensor 4 or the signal from acceleration sensor 5 exceed a given threshold. In particular, the measurement can be interrupted, measured results can be ignored or the user can be advised if it is found that the forces vary too strongly or that the acceleration is too high.

5. Temperature Sensor

Temperature sensor 6 comprises one or more temperature detectors for measuring one or more temperature parameters.

Advantageously, several temperatures are measured. These include surrounding environmental temperature, the temperature within the apparatus and on the electrode arrangement, as well as the superficial skin temperature. These measurements can be made using a range of detectors including thermocouples or infrared radiation detection methods. Intradermal temperature variations could be evaluated by observing variations in the dielectric properties of the tissue at predefined depth in the gigahertz region where the dielectric properties are mostly influenced by the properties of water, see e.g. US 2005/0083992.

Figure 12:
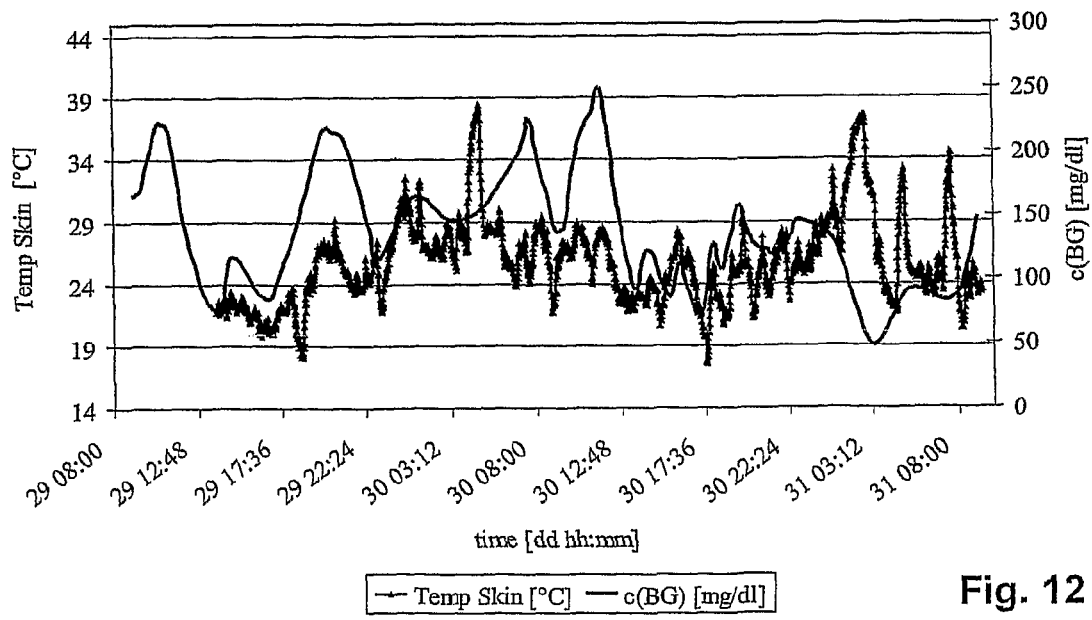
FIG. 12 shows skin temperature and glucose profile over several days in a patient with Type 1 diabetes.

The graph presented in FIG. 12 shows a glucose profile of a type 1 diabetes patient together with skin temperature measured with a Pt 1000 element mounted on a sensor plate with skin contact. The patient was following regular daily activities and controlled his blood glucose with regular insulin injections according to measurements performed with an invasive blood glucose monitoring device. It has been reported before that various body temperatures, including skin temperature, can be used for glucose approximation in patients with diabetes. However, as can be seen from FIG. 12, there is very little direct agreement between blood glucose measurements and skin temperature. In other words, if there were a correlation between the two parameters, it is highly perturbed by the influence of external temperature factors and its impact on skin temperature as well as body temperature, which is regulated according to temperature challenges introduced by the surrounding temperature. This effect is also reflected in changes in microvascular perfusion and has been studied in great detail by various groups. Hence there is a great interest to measure body temperatures including skin temperature for compensation of other glucose related signals, such as impedance or optical based glucose signals.

6. Inductive Detection Device

The inductive detection device 8 comprises at least one electric coil and a current source for generating a non-constant current therein. This current gives rise a magnetic field in the tissue, the response of which can be used to determine a parameter depending, inter alia, on glucose concentration. Suitable devices are described in EP1220638 or WO 04/028358. It can provide a further parameter depending on the glucose concentration and/or other relevant state variables of the tissue.

7. Ultrasonic Detector

The present apparatus can also comprise an ultrasonic detector. Such an ultrasonic detector, which measures the speed of sound in the blood or tissue, can provide further information on the glucose level, as e.g. described in WO 2005/017642.

8. Evaluation Circuitry

Evaluation circuitry 1 combines the signals of the sensor modules 2-8 to obtain a measure of the glucose level in the tissue. As mentioned, a general algorithm and calibration method to be used for evaluating the signals is described in WO 2005/053526, in particular in the sections "Calibration" and "Normal Operation" thereof, the disclosure of which is incorporated herein.

8.1 Improvements

In the following, we describe some refinements to the algorithm used by the evaluation circuitry of the apparatus to determine the glucose level. Basically, an advantageous algorithm can be divided up in two parts. For convenience, we refer to these two parts as the fundamental analysis and the technical analysis, respectively. The main part of the algorithm is the fundamental analysis that tales place in three steps.

The Three Steps Are:
1. Solution of the electromagnetic inverse scattering problem
2. Correction of the signal to eliminate perturbation effects
3. Transformation of the corrected signal into a glucose concentration.

Here, electromagnetic inverse scattering designates the mathematical method that transforms the scattered electromagnetic wave fields into information about the dielectric properties of the skin and underlying tissue, i.e., into information about the conductivities and permittivities characterizing the multi-layer skin system. Since, it is assumed that these dielectric properties are affected by a change of the glucose concentration, the conductivities and permittivities can be used as a measure of the glucose concentration, provided that the functional relation between the glucose concentration and the dielectric properties of the skin is known at least empirically.

However, the dielectric properties of the skin and underlying tissue are not only affected by the value and/or variations of glucose, but also by a variety of other effects, such as temperature variations, sweat variations, moisture migration in skin or changes in the blood microcirculation, perfusion characteristics, change of the tissue to sensor contact pressure, etc. Here, all effects and factors that are not in connection with the primary interaction between glucose and dielectric properties, i.e., with the primary detection process, are considered as perturbation effects. In the algorithm we distinguish between such perturbation effects and glucose effects, which then refer to effects that are related to the primary detection process. Accordingly, the conversion of the dielectric properties of the skin and underlying tissue into a glucose concentration is carried out in two steps. First, a compensation of the perturbation effects is carried out in step 2, so that the remaining variation observed in the dielectric parameters can be attributed, to a glucose change. The corresponding conversion of the corrected (i.e. compensated) dielectric parameters into a glucose concentration is then carried out in step 3.

In order to be able to carry out step 2 and 3 one has to determine the functional relation between the dielectric tissue parameters and the perturbation effects as well as the glucose effects.

Principally, this functional relation can be derived by means of a statistical procedure; namely, the well known multiple regression (see e.g. Hüsler & Zimmermann 2001).

The technical analysis is dedicated to the analysis of glucose time series. The goal is to identify patterns, regularities and statistical laws characterizing the evolution of the glucose concentration over time. These laws can then be used to make predictions about the glucose concentration in the near future based on the knowledge of the concentrations in the past. It is not expected that the technical analysis can make precise predictions, but it may be possible to narrow down the range of possible concentrations in the near future. Thus, the technical analysis has only a complementary and supportive character.

8.2 Calibration

Again, the basic calibration algorithm has been described in the section "Calibration" of WO 2005/053526 and is incorporated herein by reference. In the following, some improvements over that algorithm are described.

During the development phase of the algorithm, the data for the multiple regression analysis should be collected repeatedly for several subjects. Then, using the same general form of the regression model, the regression is carried out for each patient individually, so that an individual set of the free model parameter (regression parameters) is obtained for each subject. Applying the appropriate statistical significance tests, we check for each parameter if it significantly differs from subject to subject or from subject group to subject group. If no significant differences in the parameter sets are found one can operate with a global parameter set, i.e., with the mean built over all parameter sets. If some of the model parameters vary significantly from subject group to subject group, for each of these groups one has to determine the corresponding representative group parameter, which are simply obtained by averaging over the group members. Finally, if some of the parameters alter significantly from subject to subject, an individual calibration, (i.e. regression) has to be carried out for each subject in order to determine the corresponding individual parameters. An element of these calibrations may need to be dynamic as well to take into account biophysical cycles in the measured tissue. Also, if the apparatus is to be used during daily activities, at least part of the calibration parameters should also be recorded during such daily activities.

8.3 Further Experimental Data

Figure 13:
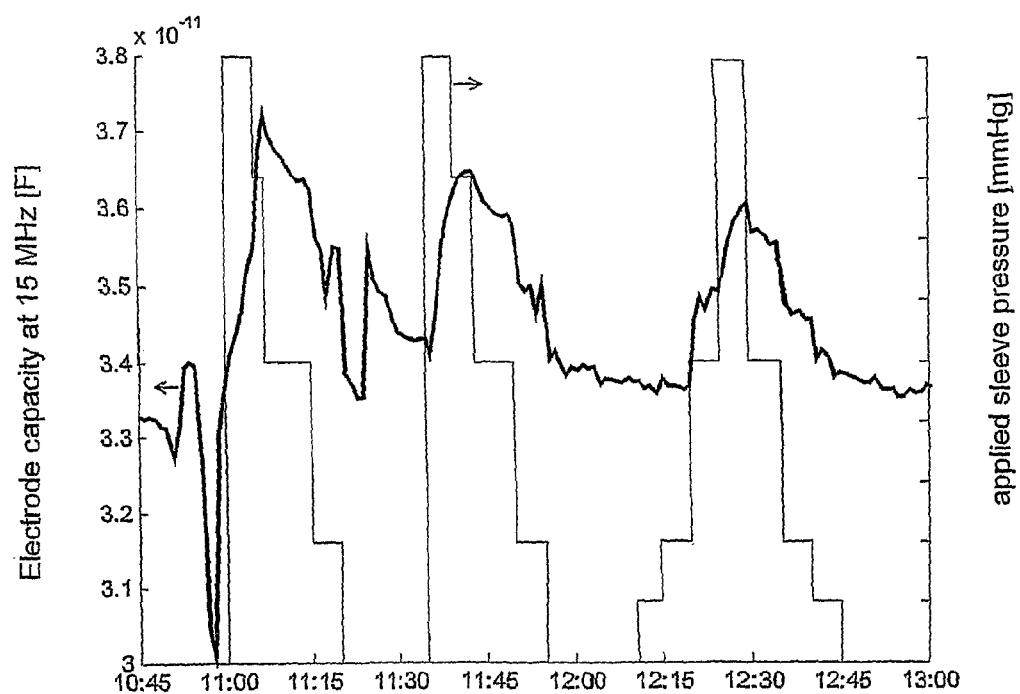
FIG. 13 shows the dependence of the electrode capacity (fat line) at 15 MHz for different sleeve pressures (thin line)
Figure 14:
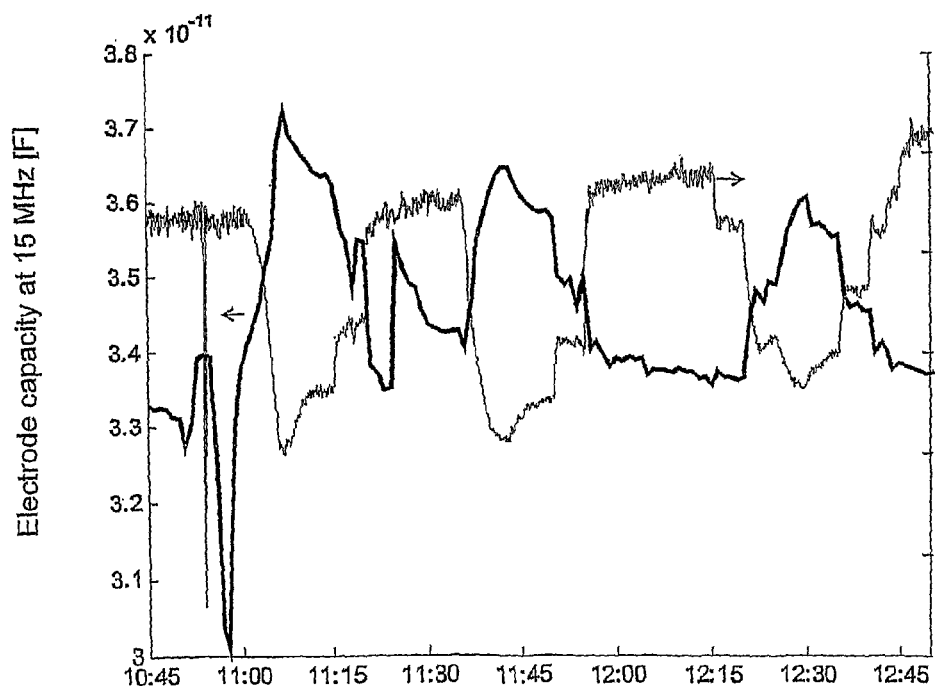
FIG. 14 shows, for the experiment of FIG. 13, the optical reflectivity (thin line) at 550 nm together with the electrode capacity (fat line)
Figure 15:
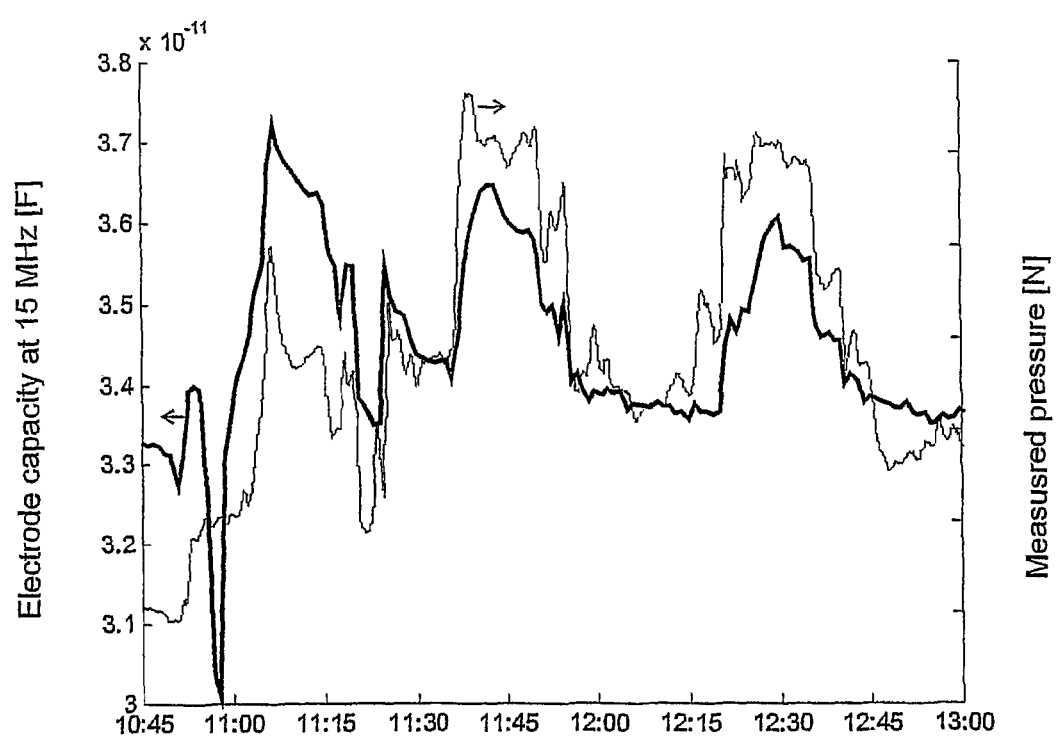
FIG. 15 shows, again for the experiment of FIG. 13, the force measured by the force sensor (thin line) together with the electrode capacity (fat line).

FIGS. 13-15 show a single experiment where a tourniquet has been applied to a patient's upper arm while measurements with the electrical detection device 2, the optical detection device 3 and the force sensor 4 were carried out. The pressure applied by the tourniquet is shown in FIG. 13. The capacity measured by the electrical detection device is shown in all figures. The optical reflectivity is shown in FIG. 14 and the force measured by the force sensor is shown in FIG. 15.

As can be seen, an increase of blood perfusion induced by the tourniquet affects all signals differently, which allows perfusion-related effects in the signals to be eliminated at least in part.

REFERENCES

1. American Diabetes Association, 1999. Clinical practice recommendations 1999, Diabetes Care 22:S77-S78.
2. The Diabetes Control and Complications Trial Research Group, 1993. The effect of intensive treatment of diabetes on the development and progression of long-term complications in insulin-dependent diabetes mellitus. N Engl J Med 329:977-986.
3. Shamoon, H., 2000. Continuous glucose monitoring: the next step towards closing the loop. Diabetes Technol Ther 2:57-59.
4. Bode, B W., Gross, T M., Thornton, K R., Mastrototaro, J J., 1999. Continuous glucose monitoring used to adjust diabetes therapy improves glycosylated haemoglobin: a pilot study. Diabetes Res Clin Prac 46:183-190.
5. Cheyne E., Kerr, D., 2002. Maling 'sense' of diabetes: using a continuous glucose sensor in clinical practice. Diabetes Metab Res Rev 18 (Suppl 1):S43-S48.
6. Khalil, O S., 2004. Non-invasive glucose measurement technologies: an update from 1999 to the dawn of the new millennium. Diabetes Technol Ther. October; 6(5):660-97.
7. Hoeber, R., 1910. Eine Metode, die elektrische Leitfaehigkeit im Inner von Zellen zu messen. Pfluegers Arch. Gesamte Physiol. Menschen Tiere. 133, 237.
8. Hoeber, R., 1910. Eine zweites Verfahren die Leitfaehigkeit im Inner von Zellen zu messen. Pfluegers Arch. Gesamte Physiol. Menschen Tiere. 133, 237.
9. Fricke, H., 1925. The electric capacity of suspensions with special reference to blood. J. Gen. Physiol. 9, 137-152.
10. Martinsen, Ø. G., Grimnes, S., Schwan, H. P., 2002. Interface phenomena and dielectric properties of biological tissue. Encyclopedia of Surface and Colloid Science, 2643-2652.
11. Schwan, H. P., 1957. Electrical Properties of Tissue and Cell Suspensions. In Advances in Biological and Medical Physics; Lawrence, J. H., Tobias, C. A., Eds.; Acad. Press: New York; Vol. V, 147-209.
12. Pethig R, Kell D B. The passive electrical properties of biological systems: their significance in physiology, biophysics and biotechnology. Phys Med Biol. 1987 August; 32(8):933-70.
13. Schwan H P., 1993. Mechanisms responsible for electrical properties of tissues and cell suspensions. Med Prog Technol.-94; 19(4):163-5.
14. Caduff A., Hirt E., Feldman Y., Ali Z., Heinemann L., 2003. First human experiments with a novel non-invasive, non-optical continuous glucose monitoring system. Biosensors and Bioelectronics 19: 209-217.
15. Alavi, S. M.; Gourzi, M.; Rouane, A.; Nadi, M.; 2003. An original method for non invasive glucose measurement: Preliminar results. 23rd Annual International Conference of the IEEE Engineering in Medicine and Biology Society, Istanbul; Turkey.
16. Gourzi M. et al., 2003. Study of a new electromagnetic sensor for glycaemia measurement. Journal of Medical Engineering & Technology. Number 627, 276-281.
17. Park, J H., Kim, C S., Choi, B C., Ham, K Y., 2003. The correlation of the complex dielectric constant and blood glucose at low frequency. Biosens Bioelectron. December 15; 19(4):321-4.
18. Fuchs K., Kaatze U., 2001. Molecular dynamics of carbohydrate aqueous solutions. Dielectric relaxation as a function of glucose and fructose concentration. J Phys Chem B 105:2036-2042.
19. Hillier, T A., Abbott, R D., Barrett, E J., 1999. Hyponatremia: evaluating the correction factor for hyperglycemia. Am J Med. April; 106(4):399-403.

20. Hayashi Y., Livshits L., Caduff A., Feldman Y., 2003. Dielectric spectroscopy study of specific glucose influence on human erythrocyte membranes. J Phys D: Appl Phys 36:369-374.
21. Caduff, A., Livshits, L., Hayashi, Y., Feldman, Yu.; 2004. Cell Membrane Response on d-Glucose Studied by Dielectric Spectroscopy. Erythrocyte and Ghost Suspensions. J Phys Chem B: 108, 13827-30.
22. Zavodnik, I B., Piasecka, A., Szosland, K., Bryszewska, M., 1997. Human red blood cell membrane potential and fluidity in glucose solutions. Scand J Clin Lab Invest. February; 57(1):59-63.
23. Roe, M W., Mertz, R J., Lancaster, M E., Worley, J F., Dules, I D., 1994. Thapsigargin inhibits the glucose-induced decrease of intracellular Ca2+ in mouse islets of Langerhans. Am J Physiol. June; 266(6 Pt 1):E852-62.
24. Pfutzner, A., Caduff, A., Larbig, M., Schrepfer, T., Forst, T., 2004. Impact of posture and fixation technique on impedance spectroscopy used for continuous and non-invasive glucose monitoring. Diabetes Technol Ther. August; 6(4):435-41.

Remark

While there are shown and described presently preferred embodiments of the invention, it is to be distinctly understood that the invention is not limited thereto but may be otherwise variously embodied and practiced within the scope of the following claims.

The invention claimed is:

1. An apparatus for determining a glucose level in body tissue or blood comprising
    an electrical detection device having an electrode arrangement for applying an electric field to the tissue or blood for measuring at least one first parameter describing a response of said tissue or blood to said electric field,
    an optical detection device comprising a light source and a light detector for measuring at least one second parameter describing a transmission or reflection of light by said tissue or blood, and
    evaluation circuitry for determining the glucose level from a combination of said first and second parameter,
    wherein the electrode arrangement comprises a plurality of parallel strip electrodes arranged to have gaps between each parallel strip electrode,
    wherein said optical detection device is disposed behind the electrode arrangement such that the light source emits light through the gaps in said electrode arrangement and the light detector measures light transmitted through the gaps in said electrode arrangement for measuring said second parameter in a part of said tissue or blood experiencing said electric field.

2. The apparatus of claim 1 further comprising an AC voltage source for applying voltages of different frequencies to said electrode arrangement.

3. The apparatus of claim 1 wherein said optical detection device is adapted to determine said second parameter for at least a first and a second wavelength.

4. The apparatus of claim 3 wherein said first wavelength is in the visible spectrum.

5. The apparatus of claim 3 wherein said second wavelength is in the near infrared spectrum.

6. The apparatus of claim 1 wherein said optical detection device comprises a waveguide for transmitting incoming and/or outgoing light.

7. The apparatus of claim 6 wherein said electrode arrangement is planar and has a first surface for facing said body tissue or blood and a second opposite surface, wherein said waveguide is located at said second surface.

8. The apparatus of claim 1 further comprising a light emitting waveguide traversing the electrode arrangement and having surface gratings in the gaps between the electrode arrangement for decoupling light emitted from the light source and projecting said light onto said tissue or blood experiencing said electric field.

9. The apparatus of claim 1 further comprising a light detecting waveguide traversing the electrode arrangement and having surface gratings in the gaps between the electrode arrangement for coupling light reflected from said tissue or blood experiencing said electric field and projecting said reflected light onto the light detector.

10. The apparatus of claim 1, wherein the structural arrangement of the electrical detection device with respect to the optical detection device enables measurements to be taken in a same physical volume of body tissue or blood.

11. An apparatus for determining a glucose level in body tissue or blood comprising
    an electrical detection device having an electrode arrangement for applying an electric field to the tissue or blood for measuring at least one first parameter describing a response of said tissue or blood to said electric field,
    an optical detection device comprising a light source and a light detector for measuring at least one second parameter describing a transmission or reflection of light by said tissue or blood, and
    evaluation circuitry for determining the glucose level from a combination of said first and second parameter,
    wherein the electrode arrangement comprises a plurality of electrodes arranged to have a plurality of parallel gaps between them,
    wherein said optical detection device is disposed behind the electrode arrangement such that the light source emits light through the gaps in said electrode arrangement and the light detector measures light transmitted through the gaps in said electrode arrangement for measuring said second parameter in a part of said tissue or blood experiencing said electric field.

12. An apparatus for determining a glucose level in body tissue or blood comprising
    an electrical detection device having an electrode arrangement for applying an electric field to the tissue or blood for measuring at least one first parameter describing a response of said tissue or blood to said electric field,
    an optical detection device comprising a light source and a light detector for measuring at least one second parameter describing a transmission or reflection of light by said tissue or blood, and
    evaluation circuitry for determining the glucose level from a combination of said first and second parameter,
    wherein the electrode arrangement comprises a plurality of electrodes arranged in a plane to have a plurality of parallel gaps between them,
    wherein said optical detection device is located at a distance from said plane of the electrode arrangement such that the light source emits light through the gaps in said electrode arrangement and the light detector measures light transmitted through the gaps in said electrode arrangement for measuring said second parameter in a part of said tissue or blood experiencing said electric field.

* * * * *